United States Patent [19]
Zimmerman

[11] Patent Number: 5,499,065
[45] Date of Patent: Mar. 12, 1996

[54] DEVICE FOR PREVENTING EYE DROPS FROM ENTERING THE NASOLACRIMAL DUCT SYSTEM

[76] Inventor: Thom J. Zimmerman, 389 Mockingbird Valley Rd., Louisville, Ky. 40207

[21] Appl. No.: 492,623

[22] Filed: Jun. 20, 1995

[51] Int. Cl.⁶ .............................. A61B 3/00; A61M 35/00
[52] U.S. Cl. ................................ 351/200; 604/1
[58] Field of Search .................... 351/200; 604/1, 604/10, 337, 393; 606/159, 204.25

[56] References Cited

U.S. PATENT DOCUMENTS

| | | | |
|---|---|---|---|
| 580,954 | 4/1897 | Ray | 128/346 |
| 2,488,616 | 11/1949 | Browne | 128/345 |
| 3,349,771 | 10/1967 | Baer | 128/325 |
| 4,299,005 | 11/1981 | Brown | 15/224 A |
| 4,457,756 | 7/1984 | Kern et al. | 604/286 |
| 4,883,454 | 11/1989 | Hamburg | 604/1 |
| 4,994,751 | 2/1991 | Cook et al. | 128/771 X |

Primary Examiner—William L. Sikes
Assistant Examiner—Huy Mai
Attorney, Agent, or Firm—Wheat, Camoriano, Smith & Beres

[57] ABSTRACT

A device for preventing eye drops disposed in the human eye from entering the nasolacrimal system includes at least one pad to be located over the exterior surface of the inside corner of an eye covering the juncture of the upper and lower eyelids of the eye in the area of the nasolacrimal ducts located on the inner surfaces of the upper and lower eyelids of the eye for occluding the nasolacrimal ducts while allowing the eye to remain open so that eye drops can be deposited in the eye.

3 Claims, 1 Drawing Sheet

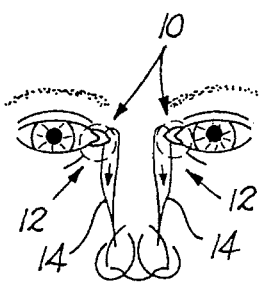
FIG. 1
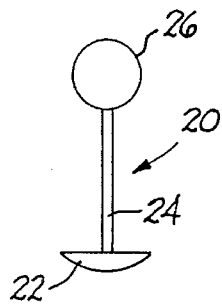
FIG. 2
FIG. 3
FIG. 4
FIG. 5
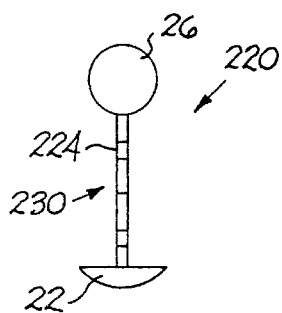
FIG. 6
FIG. 7
FIG. 8
FIG. 9
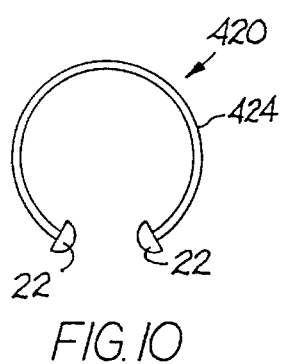
FIG. 10
FIG. 11
FIG. 12
FIG. 13

5,499,065

DEVICE FOR PREVENTING EYE DROPS FROM ENTERING THE NASOLACRIMAL DUCT SYSTEM

BACKGROUND OF THE INVENTION

The present invention relates to devices for covering at least a portion of the human eyelid, and more particularly, to a device to be located over the exterior surface of the inside or medial corner of an eye covering the juncture of the upper and lower eyelids in the areal of the nasolacrimal ducts.

Eye drops are designed to be absorbed through the front surface of the eye. The longer the medicine remains in contact with the eye, the better it is absorbed. Up to 90% of a drop, however, can be pumped away through the nasolacrimal duct before it has a chance to be absorbed into the eye.

Various studies have been made to determine the effects of different techniques of applying eye drops to the human eye. One such study is entitled, "Improving the Therapeutic Index of Topically Applied Ocular Drugs" and was published in the "Archives of Ophthalmology" April 1984, Volume 102 copyrighted by the American Medical Association. The concluding statement of this publication stated that, "In our experiments, we have observed a considerable reduction of systemic absorption of topical timolol by the simple procedures of NLO (nasolacrimal duct occlusion) (67% reduction) . . . Furthermore, these procedures increase the maximal concentration of fluorescein in the anterior chamber. These maneuvers increase corneal contact time and decrease the amount of drug delivered to the nasopharyngeal mucosa. Although only timolol and fluorescein were used in these experiments, theoretically, all topically applied drugs should manifest similar behavior. Generally, decreasing the amount of drug presented to the nasopharyngeal mucosa will decrease the systemic blood concentration of that drug. Similarly, prolonged corneal contact time will probably elevate intraocular concentration of a drug. Variability of dose-response curves and the bioavailability of a drug at receptor sites determine the degree to which ocular and systemic side effects are manifested.

Furthermore, . . . NLO . . . increased anterior chamber fluorescein concentration and duration of fluorescence. In most cases, this would allow a marked reduction of the applied concentration of the drug without loss of the desired ocular effect or duration of that effect and a further decrease in the possibility of systemic side effects. If the concentration cannot be decreased because of decreased desired effect, perhaps these procedures might permit a decrease in frequency of application.

With these techniques, even drugs contraindicated because of systemic side effects may be used with precautions, e.g., timolol in patients with asthma or epinephrine in patients with hypertension. Such clinical trials are underway.

In summary, five minutes of NLO . . . potentially improves the efficacy and potentially decreases the associated system side effects of topically applied ocular drugs."

By occluding the nasolacrimal duct for five minutes, the contact time of the drug to the ocular surface was greatly increased and significantly increased the penetration into the eye. This not only increases the intended effect of the drug but, by decreasing the amount of medication entering the blood stream through the nasopharyngeal surface, it also reduces the potential for systemic side effects.

The heretofore recommended technique of applying eye drops to the eye and performing nasolacrimal duct occlusion (NLO) is to apply a single eye drop to the open eye immediately place the forefinger over the upper eyelid one finger's breadth from the base of the nose and apply enough pressure downwardly to keep the eyelid firmly closed for at least, and preferably, five minutes.

A problem with this technique is that it requires an ophthalmologist significant time (10–15 minutes) to teach this technique to a patient. Even more importantly, typical patients resist using this technique because the technique is very difficult to perform properly and requires a relatively high level of dexterity. This is particularly difficult for older persons.

There are no devices known to me for preventing eye drops from entering the nasolacrimal duct system.

SUMMARY OF THE INVENTION

The present invention provides a device for preventing eye drops from entering the nasolacrimal duct system by occluding the nasolacrimal ducts. The device requires very little time to learn to use.

The present invention further provides a device of the class described which does not require any significant level of manual dexterity to use.

More particularly, the present invention provides a device for preventing eye drops disposed in the human eye from entering the nasolacrimal system. The device comprises pads to be positioned over the exterior surface of the inside or medial corner of an eye covering the juncture of the upper and lower eyelids of the eye in the area of the nasolacrimal ducts located on the inner surfaces of the upper and lower eyelids of the eye. The pads are applied with sufficient pressure to occlude the nasolacrimal ducts.

BRIEF DESCRIPTION OF THE DRAWINGS

The present invention will become even more clear upon reference to the following description in combination with the accompanying drawings, wherein like numerals refer to like parts throughout and in which:

FIG. 1 is a schematic representation of a human face illustrating the nasolacrimal ducts;

FIG. 2 is a schematic front view of one embodiment of the device of the present invention;

FIG. 3 is a side view of the device of FIG. 2;

FIG. 4 is a schematic front view of another embodiment of the device of the present invention;

FIG. 5 is a side view of the device of FIG. 4;

FIG. 6 is a schematic front view of still another embodiment of the device of the present invention;

FIG. 7 is a side view of the device of FIG. 6;

FIG. 8 is a schematic front view of yet another embodiment of the device of the present invention;

FIG. 9 is a side view of the device of FIG. 8;

FIG. 10 is a schematic front view of a further embodiment of the device of the present invention;

FIG. 11 is a side view of the device of FIG. 10;

FIG. 12 is a schematic front view of still a further embodiment of the device of the present invention; and FIG. 13 is a side view of the device of FIG. 12.

DETAILED DESCRIPTION OF THE PREFERRED EMBODIMENTS

With reference to FIG. 1, there is shown a schematic representation of a human face illustrating the nasolacrimal ducts, generally denoted as the numeral 10 which extend from the inner surfaces of the upper and lower eyelids at the inside or medial corner 12 of the eye. The upper and lower ducts 10 communicate with the nasal passages 14.

With reference to FIGS. 1 and 2, there is shown a device, generally denoted as the numeral 20 of the present invention for preventing eye drops deposited in the human eye from entering the nasolacrimal system.

The device 20 comprises a pad 22 mounted to one end of a rod 24 with a small finger grasp handle 26 attached to the opposite end of the rod 24. The pad 22 is sized and configured to be positioned over the exterior surface of the inside or medial corner area 12 of an eye and cover the juncture of the upper and lower eyelids in the area of the nasolacrimal ducts 10 located on the inner surfaces of the upper and lower eyelids. More preferably, the pad 22 also covers the area between the inside or medial corner 12 of the eye and the adjacent side of the nose as indicated by the phantom lines in FIG. 1.

The pad 22 is fabricated of a soft resilient material so as not to bruise the skin. In addition, the rod 24 is fabricated of a resilient flexible material such as a plastic which is impervious to liquid.

In use, the handle 26 is gripped by, for example, the thumb and index finger and positioned with the pad 22 against the medial corner 12 of the open eye and pushed against the inner corner 12 of the eye with a gentle force sufficient to occlude the nasolacrimal ducts 10. The flexible rod 24 may bend somewhat as the force is applied to generate a constant gentle pressure biasing the pad 22 against the medial corner of the eye sufficient to occlude the nasolacrimal ducts or passages 10.

With reference to FIGS. 4 and 5, there is shown a device, generally denoted as the numeral 120 of the present invention which is identical to the device 20 of FIGS. 2 and 3 in most respects. For the sake of brevity, the common components are identified by identical numerals and the description thereof will not be repeated. The device 120 further includes hinge means 28 interconnecting the pad 22 to the end of the rod 24 so that the pad 22 can pivot about the hinge means 28 to orient with the contour or curvature of the facial bone structure between the medial corner of the eye and the nose. The device 120 is used in the same manner as the device 20 discussed above. And, therefore, for the sake of brevity, the description will not be repeated.

Now with reference to FIGS. 6 and 7, there is shown a device, generally denoted as the numeral 220 of the present invention for preventing eye drops deposited in the human eye from entering the nasolacrimal system.

The device 220 comprises a pad 22 mounted to one end of a rod 224 with a small finger grasp handle 26 attached to the opposite end of the rod 224. The rod 224 differs from the rod 24 of the device 20 of FIG. 2 in that the rod 224 further comprises biasing means 230 located between the handle 26 and pad 22. The biasing means 230 can be a compression spring either as a separate component from the rod 224 and attached thereto, or as shown, the spring can be integrally formed with the rod 224 by essentially bending the rod 224 in a serpentine path. The device 220 is used in the same manner as the device 20 discussed above and, therefore, for the sake of brevity the description will not be repeated.

With reference to FIGS. 8 and 9, there is shown a device, generally denoted as the numeral 320, of the present invention for preventing eye drops deposited in the human eye from entering the nasolacrimal system.

The device 320 comprises two pads 22, each pad 22 to be positioned over the exterior surface of the inside or medial corner of a different one of the eyes covering the junction of the upper and lower eyelids in the area of the nasolacrimal ducts located on the inner surfaces of the upper and lower eyelids as discussed above in regard to the pad 22 of the device 20 and 120 of FIGS. 2–7. The pads 22 are interconnected with each other by a U-shaped rod 324 with the pads 22 connected to the ends of the legs of the U-shaped rod 324. A handle 26 is attached to the U-shaped rod 324 midway between the ends of the U-shaped rod 224 and projects outwardly from the convex side of the U-shaped rod 224. The U-shaped rod 224 can be fabricated of a resilient flexible material as with the rod 24 of the device 10. Alternatively, as shown in FIGS. 8 and 9, each leg of U-shaped rod 324 comprises biasing means 330 located between the handle 26 and pad 22. The biasing means 328 is shown as a springs formed by bending the legs of the U-shaped rod 324 in a serpentine path.

In use, the handle 26 is gripped by, for example, the thumb and index finger and is positioned with the U-shaped rod 324 over and across the bridge of the nose and with each pad 22 positioned over the exterior surface of the inside or medial corner of a different one of the eyes. The pads 22 are pushed against the inside or medial corners of the eye with a gentle force sufficient to occlude the nasolacrimal ducts 10 of both eyes.

With reference to FIGS. 10 and 11, there is shown a device, generally denoted as the numeral 420, of the present invention for prevent eye drops from entering the nasolacrimal system.

The device 420 comprises two pads 22, each pad 22 to be positioned over the exterior surfaces of the inside or medial corners of a different one of the eyes covering the juncture of the upper and lower eyelids in the area of the nasolacrimal ducts located on the inner surfaces of the upper and lower eyelids as discussed above in regard to the device 320 of FIGS. 8 and 9. The pads 22 are interconnected with each other by a C-shaped rod 424 with the pads 22 connected to the ends of the C-shaped rod 424. The C-shaped rod 424 is fabricated of a resilient, flexible material. In use of the device 420, the C-shaped rod 424 is located over and across the bridge of the nose by displacing the pads 22, and, therefore, the ends of the C-shaped rod 424 away from each other, positioning the pads 22 over the exterior surface of the inside or medial corners of different eyes. When the pads 22 are in position, the resilient C-shaped rod 424 forces the pads 22 generally toward each other. The C-shaped rod 424 is configured, sized, and has a modular of elasticity to force the pads 22 generally toward the nose and against the inside corners of the eyes with a constant force to generate a pressure biasing the pads 22 against the inside or medial corners of the eyes sufficient to occlude the nasolacrimal ducts 10 of both eyes.

With reference to FIGS. 11 and 12, there is shown a device, generally denoted as the numeral 520 of the present invention which is identical to the device 420 of FIGS. 10 and 11 in most respects. Therefore, for the sake of brevity, the common components are identified by identical numerals and the description thereof will not be repeated. The device 520 further includes hinge means 528 interconnecting each pad 22 to a different one of the ends of the C-shaped rod 424 so that the pads 22 can pivot about the hinge means 528 to orient with the contour or curvature of the facial bone structure between the medial corner of the eyes and the bridge of the nose. The device 520 is used in the same manner as the device 420 discussed above and, therefore, for the sake of brevity the description will not be repeated.

The pads 22 can be oval in peripheral shape with a major axial dimension of, for example, about ¾ of an inch long and a minor axial dimension of, for example, about ⅜ of an inch long.

The foregoing detailed description is given primarily for clearness of understanding and no unnecessary limitations are to be understood therefrom for modifications will become obvious to those skilled in the art and may be made without departing from the spirit of the invention and scope of the appended claims.

I claim:

1. A device for preventing eye drops disposed in the human eye from entering the nasolacrimal system comprising a rod comprising compression biasing means acting along the axis of the rod;

pad means mounted to one end of said rod and sized and configured to cover the exterior surface of the medial corner of an eye covering the juncture of the upper and lower eyelids of the eye in the area of the nasolacrimal ducts located on the inner surfaces of the upper and lower eyelids of the eye for occluding the nasolacrimal ducts when the pad means is positioned over the juncture of the upper and lower eyelids; and a handle attached to the opposite end of said rod.

2. The device of claim 1 comprising hinge means interconnecting the pad means to said one end of the rod.

3. A device for preventing eye drops disposed in the human eye from entering the nasolacrimal system, comprising a pair of pads each sized and configured to cover the exterior surfaces of the medial corner of respective eyes and covering the juncture of the upper and lower eyelids in the area of the nasolacrimal ducts located on the inner surfaces of the upper eyelids of both eyes, and an arcuate, resilient and flexible rod having a pair of ends, each end of said rod connected to a respective pad by a hinge means, said arcuate rod being sized and configured to fit over the bridge of a nose of a user and exerting sufficient medial pressure to occlude the nasolacrimal duct.

* * * * *